United States Patent
Sain et al.

(10) Patent No.: US 6,740,619 B1
(45) Date of Patent: May 25, 2004

(54) PROCESS FOR THE PREPARATION OF A CATALYST USEFUL FOR LIQUID-LIQUID SWEETENING LPG AND LIGHT PETROLEUM DISTILLATES

(75) Inventors: Bir Sain, Dehradun (IN); Som Nath Puri, Dehradun (IN); Gautam Das, Dehradun (IN); Bhagwati Prasad Balodi, Dehradun (IN); Sunil Kumar, Dehradun (IN); Anil Kumar, Dehradun (IN); Virendra Kumar Kapoor, Dehradun (IN); Virendra Kumar Bhatia, Dehradun (IN); Turuga Sundara Rama Prasada Rao, Dehradun (IN); Gur Pratap Rai, Mumbai (IN)

(73) Assignee: Council of Scientific and Industrial Research, New Delhi (IN)

( * ) Notice: Subject to any disclaimer, the term of this patent is extended or adjusted under 35 U.S.C. 154(b) by 407 days.

(21) Appl. No.: 09/804,994

(22) Filed: Mar. 13, 2001

(30) Foreign Application Priority Data

Nov. 17, 2000 (IN) .................................. 1032/DEL/2000

(51) Int. Cl.$^7$ .......................... B01J 31/00; C10G 19/00
(52) U.S. Cl. ...................................... 502/163; 208/203
(58) Field of Search ........................... 502/163; 208/203

(56) References Cited

U.S. PATENT DOCUMENTS

| | | | |
|---|---|---|---|
| 5,135,717 A | * 8/1992 | Renzoni et al. | 422/61 |
| 5,149,800 A | * 9/1992 | Kluger et al. | 540/123 |
| 5,248,538 A | * 9/1993 | Kovacs et al. | 428/64.8 |
| 5,346,670 A | * 9/1994 | Renzoni et al. | 422/52 |
| 5,359,056 A | * 10/1994 | Kaieda et al. | 540/137 |
| 6,444,807 B1 | * 9/2002 | Wolleb et al. | 540/131 |
| 6,565,740 B2 | * 5/2003 | Sain et al. | 208/203 |

* cited by examiner

*Primary Examiner*—Mark L. Bell
*Assistant Examiner*—Jennine M. Brown
(74) *Attorney, Agent, or Firm*—Ladas & Parry

(57) ABSTRACT

The present invention relates to a process for the preparation of metal phthalocyanine sulphonamide [$MPc(SO_2NHR)_x$] catalyst useful for sweetening of LPG and light petroleum distillates which comprises reacting a metal phthalocyanine with chlorosulphonic acid at 90–150° C. for 1–5 hrs. cooling the reaction mixture adding 1–7 parts of a chloride reagent heating the said mixture at 60–80° C. from 0.5–3 hrs. to obtain the metal phthalocyanine sulphonyl chloride, isolating it by adding the reaction mixture in ice cold water, reacting the isolated metal phthalocyanine sulphonyl chloride with an amine of general formula $H_2NR$ where R is selected from hydrogen, aryl, alkyl and cycloalkyl in an aqueous or non-aqueous medium or a mixture thereof at a temperature in the range −4 to 15° C. and at a pH ranging between 7–9 in the presence of an acid binding agent to obtain the described metal phthalocyanine sulphonamide catalyst wherein the chloride reagent used is selected from the group consisting of thionyl chloride, phosphorus trichloride and phosphorus pentachloride, the binding agent used is selected from the group consisting of sodium bicarbonate, sodium carbonate, sodium hydroxide and tertiary organic bases selected from pyridine triethyl amine and piperidine and the catalyst metal phthalocyanine sulphonamide is selected from the group consisting of cobalt, manganese, nickel, iron vanadium phthalocyanine sulfonamide most preferably cobalt phthalocyanine sulphonamide.

22 Claims, No Drawings

PROCESS FOR THE PREPARATION OF A CATALYST USEFUL FOR LIQUID-LIQUID SWEETENING LPG AND LIGHT PETROLEUM DISTILLATES

The present invention relates to an improved process for the preparation of a catalyst useful for liquid-liquid sweetening of LPG and light petroleum distillates.

More particularly the invention relates to the preparation of sulphonamides of various metal phthalocyanines suitable as catalysts and their use for liquid-liquid sweetening of pentanes, LSRN, cracked naphtha and regeneration of alkali in the extraction of mercaptans from LPG, pentanes, LSRN and light thermally cracked naphtha.

It is well known that the presence of mercaptans in the petroleum products like LPG, naphtha, gasoline, kerosene, ATF etc is highly undesirable because of their foul odour and highly corrosive nature. They are also poisonous to the catalysts and adversely affect the performance of tetraethyl lead as octane booster. Although there are several processes known for the removal of mercaptans from petroleum products, the most common practice is to oxidize the mercaptans present to less deleterious disulphides with air in the presence of a catalyst. Generally, the lower mercaptans present in LPG, pentanes, LSRN and light thermally cracked naphtha are first extracted in alkali solution and then oxidized to disulfides with air in the presence of a catalyst. The disulphides, being insoluble in alkali solution, separate out from the top and the alkali is regenerated. In the liquid-liquid sweetening the lower mercaptans present in petroleum products like pentanes, LSRN, cracked naphtha etc are converted to disulphides by direct oxidation with air in the presence of alkali solution and catalyst. The higher molecular weight mercaptans present in petroleum products like heavy naphtha, FCC gasoline, ATF and kerosene are oxidized to disulphides with air in a fixed bed reactor containing catalyst impregnated on a suitable support like activated carbon (Catal. Rev.-Sci. Eng. 35(4), 571–609 (1993).

It is also well known that the phthalocyanines of the metals like cobalt, iron, manganese, molybdenum and vanadium catalyze the oxidation of mercaptans to disulphides in alkaline medium. Among these cobalt and vanadium phthalocyanines are preferred. As the metal phthalocyanines (MPC's) are not soluble in aqueous medium, for improved catalytic activity their derivatives like sulphonated and carboxylated metal phthalocyanines are used as catalysts for sweetening of petroleum fractions. For example use of cobalt phthalocyanine monosulphonate as the catalyst in the fixed bed sweetening of various petroleum products (U.S. Pat. Nos. 3,371,031; 4,009,120; 4,207,173; 4,028,269; 4,087,378; 4,141,819, 4,121,998; 4,124,494; 4,124,531) and cobalt phthalocyanine disulphonate (U.S. Pat. No. 4,250,022) tetra sulphonate (U.S. Pat. No. 2,622,763) and the mixture thereof (U.S. Pat. No. 4,248,694) as catalysts for liquid-liquid sweetening and alkali regeneration in mercaptan extraction of light petroleum distillates have been reported. The use of phenoxy substituted cobalt phthalocyanine as sweetening catalyst (Ger Offen 3,816,952), cobalt and vanadium chelates of 2,9,16,23-tetrakis (3,4-dicarboxybenzoyl)phthalocyanine as effective catalyst for both homogeneous and fixed bed mercaptan oxidation (Ger Offen 2,757,476; Fr. Demande 2,375,201) and cobalt, vanadium chelates of tetrapyridinoporphyrazine as active catalysts for sweetening of sour petroleum distillates (Ger offen 2,441,648) have also been reported.

It is well known that the catalysts used for the liquid-liquid sweetening of petroleum fractions like pentanes, LSRN, etc. and regeneration of alkali in the mercaptan extraction from LPG, pentanes etc are di-, tri-and tetra sulphonates of metal phthalocyanines particularly those of cobalt and vanadium phthalocyanines; cobalt phthalocyanine sulphonates being specially preferred. The cobalt phthalocyanine sulphonates differ in activity and in their solubility characteristics depending upon the number of sulphonate functionalities leading to problems in their use as catalysts.

Cobalt phthalocyanine disulphonate, a commonly used catalyst in liquid-liquid sweetening and alkali regeneration, is extremely dusty in the dry fine powder form and causes a handling problem. To overcome this problem cobalt phthalocyanine disulphonate is admixed with water and commonly used as a slurry. However, with insufficient mixing the cobalt phthalocyanine disulphonate precipitates out from the slurry. Moreover, even if the slurry is mixed sufficiently, it retains the cobalt phthalocyanine disulphonate in suspension for a particular length of time only, beyond which the slurry becomes extremely viscous and may form gel, making it very difficult to remove the material from packaging. Cobalt phthalocyanine tetrasulphonate, on the other hand, is highly soluble in water and its use can eliminate precipitation and gel forming problems associated with the use of cobalt phthalocyanine disulphonate. However, it is reported that cobalt phthalocyanine tetrasulphonate has lower catalytic activity than cobalt phthalocyanine disulphonate (U.S. Pat. No. 4,885,268). Further, preparation of the metal phthalocyanine disulphonates by reacting metal phthalocynines with oleum has handling and working-up problems.

During our investigations on the development of new sweetening catalysts, we observed metal phthalocyanine sulphonamides to be active catalysts for liquid liquid sweetening of light petroleum products (Indian Patent No 1,53,190, Indian Patent No. 1,52,541 and Ind. J. Tech. 25, 397–400 (1987)). In these patents and literature a procedure for making cobalt phthalocyanine sulphonamides has been reported. This method involves treatment of cobalt phthalocyanine with chlorosulphonic acid followed by amidation with ammonia gas. However, the catalyst yield and activity was found to be low. Hence the present invention provides an improved process for the preparation of metal phthalocyanine sulphonamides in considerably higher yields and with very high catalytic activities for both liquid-liquid sweetening and alkali regeneration.

The objective of the present invention is to provide an improved process for the preparation of metal phthalocyanine sulphonamide suitable a catalyst for liquid-liquid sweetening of pentanes, LSRN, cracked naphtha etc. and regeneration of alkali in the mercaptan extraction from LPG, pentanes, LSRN, light thermally cracked naphtha and the like, which obviates the drawbacks as detailed above.

Accordingly the present invention provides an improved process for the preparation of catalyst metal phthalocyanine sulphonamide of the formula

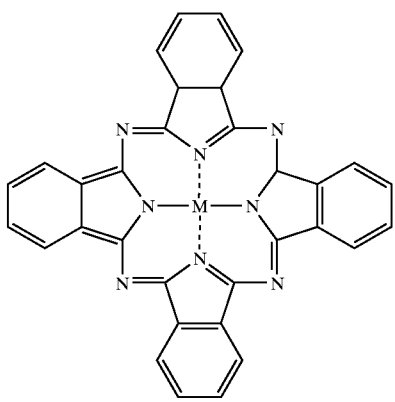

Mpc(SO$_2$NHR)$_x$
wherein MPc represents

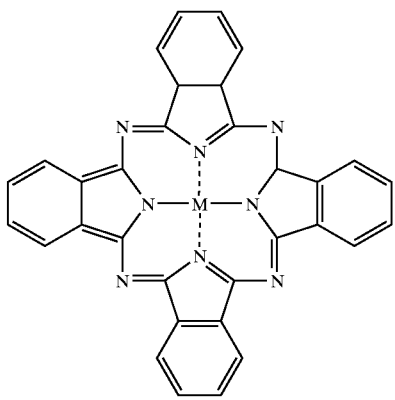

M is Co, Ni, Fe, Mn, Cr or V;
X is 1, 2, 3 or 4 and
R is hydrogen, alkyl, or cycloalkyl,
useful for LPG and light petroleum distillates which comprises;
reacting a metal phthalocyanine with chlorosulphonic acid at a temperature in the range of 90–150° C. for a period ranging between 1 hr–5 hrs, cooling the mixture to a temperature ranging between 40–80° C., adding 1–7 parts of a chloride reagent to the said mixture, heating the above said mixture to a temperature ranging between 60–80° C for a period ranging between 0.5 hr to 3 hrs to obtain the metal phthalocyanine sulphonyl chloride, isolating the above said compound by adding the reaction mixture in an ice cold water, reacting the above isolated metal phthalocyanine sulphonyl chloride with an amine of general formula H$_2$NR where R is selected from hydrogen, aryl, alkyl and cycloalkyl in an aqueous or non aqueous medium or a mixture thereof at a temperature in the range −4 to 15° C. and at a pH ranging between 7–9 in the presence of an acid binding agent to obtain the desired catalyst.

In an another embodiment of the present invention the metal phthalocyanine used is selected from the group consisting of cobalt, manganese, iron, nickel, chromium and vanadium phthalocyanine, most preferably cobalt phthalocyanine.

In yet another embodiment of the present invention the chloride reagent used is selected from thionyl chloride, phosphorus trichloride and phosphorus pentachloride.

In yet another embodiment of the present invention the non-aqueous medium used is to selected from the group consisting of chlorobenzene, nitrobenzene, alcohols and N,N--dimethylformamide.

In yet another embodiment of the present invention the acid binding agent used is selected from the group consisting of sodium bicarbonate, sodium carbonate, sodium hydroxide and tertiary organic bases selected from pyridine, triethyl amine and piperidine. In yet another embodiment of the present invention the catalyst prepared is metal phthalocyanine sulphonamide selected from the group consisting of cobalt, manganese, nickel, iron, vanadium phthalocyanine sulphomamide and their N-substituted sulphonamide derivatives, most preferably selected from cobalt phthalocyanine tetra-sulphonamide and cobalt phthalocyanine tetra-N-(4-hydroxy phenyl)sulphonamide.

In still another embodiment of the present invention the metal phthalocyanine sulphonamide catalyst is useful for both liquid-liquid sweetening and alkali regeneration in the mercaptan extraction from petroleum fraction such as LPG, pentanes, light straight run naphtha and cracked naphtha.

In the present invention the sulphonamides of the metal phthalocyanines suitable as sweetening catalysts are prepared by first converting the suitable metal phthalocyanine to the corresponding metal phthalocyanine sulphonyl chloride (mono-, di-, tri-, tetrasulphonyl metal phthalocyanine or a mixture thereof) followed by reacting the metal phthalocyanine sulphonyl chlorides with different amines including ammonia to yield the metal phthalocyanine sulphonamides.

According to the present invention one part of suitable metal phthalocyanine is slowly added to 5–20 parts of chlorosulphonic acid at room temperature. The temperature of the reaction mixture is slowly increased in stages to 90–150° C. and maintained at this temperature for 1–5 hrs. The reaction mixture is then preferably cooled to 40–80° C. and 1–7 parts of thionyl chloride or phosphorus pentachloride or phosphorus trichlonde or similar such reagent is slowly added. After this addition, in case of thionyl chloride the reaction mixture is heated to 60–80° C. and maintained at 20 this temperature for 0.5–3 hrs. In case of other reagents the reaction mixture is heated to a suitable temperature for a suitable period. The metal phthalocyanine sulphonyl chloride thus formed is isolated by any suitable technique like hydrolysing the reaction mixture with ice cold water. This yields 1.6–1.69 parts of metal phthalocyanine sulphonyl-chloride with metal phthalocyanine tetrasulphonyl chloride as major component and trisulphonyt-, disulphonyl chlorides as the minor components.

Similarly metal phthalocyanine mono-, di-, tri-, tetrasulphonic acid or mixture thereof is converted into the corresponding metal phthalocyanine sulphonyl chlorides in almost quantitative yields, by adding one part of the former to 3–8 parts of chlorosulphonic acid or similar such solvent at room temperature preferably under cooling conditions, heating the reaction mixture to 60–80° C. and then adding 1–5 parts of reagents like thionyl chloride or phosphorus pentachloride or phosphorus trichloride or the like. The reaction is completed by heating for 0.5 to 5 hrs at a suitable temperature.

The present invention provides an improved methodology for the conversion of metal phthalocyanine sulphonyl chlorides, thus obtained, in to the corresponding metal phthalocyanine sulphonamides suitable as catalysts for the liquid-liquid sweetening and alkali regeneration in the mercaptan extraction. The suitable metal phthalocyanine sulphonamides have—SO$_2$NHR group where R may be hydrogen, alkyl, cycloalkyl, aromatic or any other group like substituted aromatic or long chain alkyl with further substitution with different functional groups. The metal phthalocyanine sulphonamides with —SO$_2$NR$^1$R$^2$—, without any hydrogen attached to nitrogen, in general are not found suitable as sweetening catalysts due to their limited solubility in alkali solution. The metal phthalocyanine sulphonamides are prepared by reacting metal phthalocyanine sulphonyl chlorides with suitable amines of general formula H$_2$NR where R may be hydrogen, alkyl, cycloalkyl, aromatic or any other group either in the form of free base or in the form of their water soluble hydrochloride or any other acid salt. The reaction of metal phthalocyanine sulphonyl chlorides with amines can be carried out in aqueous or non-aqueous medium such as chlorobenzene, nitrobenzene, alcohols, or N, N-dimethylformamide in the presence of acid-binding agents. The suitable acid-binding agents are sodium bicarbonate, sodium carbonate, sodium hydroxide, tertiary organic bases such as pyridine or triethylamine or an excess of the amines used for making sulphonamide. The reaction is carried out at pH values in a weakly acidic to alkaline ranges.

The improved method of this invention for the preparation of metal phthalocyanine sulphonamides with SO$_2$NH$_2$ groups consists of dispersing the wet cake of metal phthalocyanine sulphonyl chloride in water, alcohol or their mixture or similar such medium and passing ammonia gas either after bringing the pH of the system to about 7.00 or without pH adjustment at 0–20° C. temperature till the reaction mixture is fairly alkaline. To this reaction mixture catalytic amount of any organic base like pyridine, piperidine, triethylamine, and alkali solution, either both or one of them is added. The reaction mixture is then stirred at room temperature for 10–120 minutes and at 30–90° C. for 10–60 minutes. The metal phthalocyanine sulphonamide is isolated by acidification of reaction mixture.

Various metal phthalocyanine sulphonamides specially those of cobalt, manganese, iron and vanadium prepared according to this invention were found to be active catalysts for liquid-liquid sweetening of pentanes, LSRN, cracked naphtha and the like, and regeneration of alkali in the mercaptan extraction from LPG, pentanes, LSRN, and light thermally cracked naphtha. The cobalt phthalocyanine sulphonamides prepared according to the improved process of this invention were found to be crystalline compounds unlike cobalt phthalocyanine disulphonate, which is extremely dusty, and can be handled without problems. These catalysts can be used directly by dissolving in alkali and no prior admixing with water is required. Unlike cobalt phthalocyanine tetrasulphonate, cobalt phthalocyanine sulphonamide prepared according to the improved method of this invention were found to be very active catalysts for liquid-liquid sweetening and alkali regeneration. As the metal phthalocyanine sulphonamide prepared according to this invention is insoluble in acidic media, they could be easily isolated.

The present invention provides an improved method for the preparation of suitable metal phthalocyanine sulphonyl chlorides which involves first treating the metal phthalocyanines with chlorsulphonic acid followed by addition of thionyl chloride to the reaction mixture. In place of thionyl chloride, phosphorus pentachloride or phosphorus trichloride or any other such reagent can also be used. The novelty of the present invention lies in the addition of thionyl chloride or such reagent which was found to be necessary to ensure complete conversion of all the sulphonic acid groups to sulphonyl chloride followed by ammination in a single step to get maximum yield of metal phthalocyanine sulphonamide.

The following examples are given by way of illustration and therefore should not be construed to limit scope of the present invention.

Preparation of Cobalt Phthalocyanine Sulphonyl Chloride

EXAMPLE 1

For the preparation of cobalt phthalocyanine tetrasulphonyl chloride, 30 parts by weight of cobalt phthalocyanine were slowly added with stirring to 315 parts by; weight of chlorosulphonic acid. The reaction mixture was heated to about 75° C. in one hour and from 75° C. to about 130° C. in 1.5 hours by controlling the heating rate, with constant stirring. The reaction mixture, after maintaining at 130–135° C. for additional 4 hours, was cooled to 60–65° C., and then 123 parts of thinly chloride were slowly added. The whole contents were heated to 79° C. and maintained at this temperature for 1 hour. The reaction product was cooled to room temperature and slowly added to crushed ice, keeping the temperature preferably below 5° C. The precipitated cobalt phthalocyanine sulphonyl chloride was filtered and washed thoroughly with cold water. The filtered cake was stored wet at 0° C. till further processing. The FAB mass spectral analysis of the sulphonamide prepared by using this cobalt phthalocyanine sulphonyl chloride showed that the product was largely cobalt phthalocyanine tetrasulphonyl chloride with some amounts of the tri- and disulphonyl chloride derivatives.

EXAMPLE 2

In another typical preparation of cobalt phthalocyanine sulphonyl chloride, 30 parts by weight of cobalt phthalocyanine were slowly added with stirring to 225 parts by weight of chlorosulphonic acid. The reaction mixture was heated to 70–75° C. in 1 hour and 75–135° C. in 1.5 hour by controlling the heating rates with continued stirring. The reaction mixture was then maintained at 130–135° C. for additional 4 hours and after cooling to 80° C., 90 parts of thionyl chloride were slowly added and the mixture stirred for one hour at 75–80° C. After cooling to room temperature, the reaction product was slowly added to crushed ice, the precipitated cobalt phthalocyanine tetrasulphonyl chloride was filtered and washed thoroughly with cold water. The filtered cake is not completely dried and stored at 0° C. or below till further processed.

EXAMPLE 3

In yet another typical preparation of cobalt phthalocyanine tetrasulphonyl chloride, 30 parts by weight of cobalt phthalocyanine were slowly added with stirring to 130 parts by weight of chlorosulphonic acid. The reaction mixture was gradually heated with stirring to 130–135° C. and after keeping at this temperature for 11 hours was cooled to 60–65° C. and 60 parts of thionyl chloride were slowly added. The contents were then stirred for 4 hours at 70–85° C. cooled to room temperature and slowly added to crushed ice. The precipitated cobalt phthalocyanine tetrasulphonyl chloride was filtered and washed thoroughly with water.

Preparation of Cobalt Phthalocyanine-4,4',4",4"',-tetrasulphonyl Chloride

EXAMPLE 4

In a typical preparation of cobalt phthalocyanine-4, 4',4", 4"'tetrasulphonyl chloride, 53 parts of tetrasodium salt of cobalt (II) 4,4', 4",4'"tetrasulphophthalocyanine di-hydrate [prepared from 4-sulphophthalic acid, ammonium chloride, urea and cobalt sulphate following literature procedure, Inorg Chem. 4,460 (1965)] was slowly added to 230 parts by weight of chlorosulphonic acid. The reaction mixture was then heated to 80° C. and 94 parts of thionyl chloride were slowly added. The contents were then heated at 80° C. for 3 hours, cooled to room temperature and then slowly added to crushed ice. The precipitated cobalt phthalocyanine-4,4', 4"4'"-sulphonyl chloride was filtered, washed thoroughly with ice water, filtered and stored wet at 0° C. or below till further processing.

Preparation of Cobalt Phthalocyanine Tetra-sulphonamide

EXAMPLE 5

In a typical preparation of cobalt phthalocyanine tetrasulphonamide, total wet cake of cobalt phthalocyanine sulphonyl chloride, prepared as described in the previous examples was dispersed in 900 parts of ice water and 190 parts of methanol added to get homogeneous dispersion. The reaction mixture was stirred at 5–8° C. and ammonia gas was passed till the mixture was fairly alkaline (pH 8–9). Pyridine (1.2 parts) was then added and the mixture stirred at room temperature for 20 minutes. This was followed by addition of 6 parts of 10% sodium hydroxide solution followed by stirring the reaction mixture for 40 minutes at room temperature. The contents were then heated to 80° C. and after maintaining at this temperature for 1 hour, cooled to room temperature and poured over a mixture of ice and concentrated hydrochloric acid keeping the pH fairly acidic (2–3). The precipitated cobalt phthalocyanine tetrasulphonamide was filtered, washed thoroughly with cold water and dried in vacuum oven to yield 44 gms of the product. The FAB mass spectral analysis of the sulphonamide obtained using cobalt phthalocyanine as the starting material showed the presence of tetra sulphonamide as the major isomer, followed by trisulphonamide and disulphonamide isomers.

EXAMPLE 6

In another typical experiment cobalt pathalocyanine sulphonamide was prepared as per the procedure described under example 5 but without the addition of pyridine and instead of 6 parts 10% sodium hydroxide, 10 parts of 10% sodium hydroxide were used. This also gave cobalt phthalocyanine tetrasulphonamide in comparable yields.

EXAMPLE 7

In yet another typical preparation of cobalt phthalocyanine sulphonamide, the total wet cake of cobalt phthalocyanine tetra sulphonyl chloride prepared as described under examples 1–4 was dispersed in 900 parts of ice water mixture, pH of the suspension brought to 3–4 by adding sodium hydroxide solution and ammonia gas was passed with stirring at 5–8° C. till the mixture was fairly alkaline (pH 8–9). Pyridine (1.2 parts) was then added and the contents stirred at room temperature for 30 minutes followed by addition of 6 parts of 10% sodium hydroxide solution and further stirring of the reaction mixture for 60 minutes at room temperature. The reaction mixture was then heated to 80° C., maintained at this temperature for 1 hour, cooled to room temperature and added to a mixture of ice and concentrated hydrochloric acid, keeping the pH fairly acidic (2–3). The precipitated cobalt phthalocyanine sulphonamide was filtered, washed thoroughly with cold water and dried in vacuum oven to yield 42.5 gm of the product.

Preparation of Cobalt Phthalocyanine N-(4-hydroxyphenyl)Sulphonamide

EXAMPLE 8

In the typical preparation of cobalt phthalocyanine N-(4-hydroxyphenyl)sulphonamide, total wet cake of cobalt phthalocyanine tetrasulphonyl chloride prepared as described in examples 1–4 was suspended in 500 parts of ice water mixtureand after bringing the pH to 3–4 at 0° C. with dilute sodium hydroxide solution, a neutralized solution of 23 parts by weight of 4-aminophenol in 400 parts of water and 20 parts by weight of sodium carbonate were added and the mixture stirred for 24 hours at 30–35° C. and another 2 hours at 60–65° C. The mixture was then acidified with hydrochloric acid. The precipitated product was filtered and dried.

Performance of evaluation of the catalyst in Liquid-Liquid Sweetening

Performance evaluation of cobalt phthalocyanine tetra-sulphonarnide catalyst prepared from cobalt phthalocyanine was carried out in the laboratory using 100-ml naphtha in each batch. The experimental set up used consisted of a 250 ml round bottom flask, fitted with a mechanical stirrer with Teflon blade, a gas inlet tube and a condenser.The feed was prepared by adding standard 1-hexanethiol to light naphtha (bp. 60–90° C.) and its mercaptan sulphur content was estimated by UOP method 163–89.For preparing the catalyst solution, cobalt phthalocyanine tetrasulphonamide[0.2 gm] was dissolved in 100 ml of 7% aqueous sodium hydroxide solution. Three ml of this catalyst solution was diluted to 20 ml with 7%-aqueous sodium hydroxide solution. The prepared feed (100 ml) was taken in the RB flask and the diluted catalyst solution (20 ml) added to it. This gave the catalyst concentration of 81.5 ppmw on feed basis. The stirrer (speed 1600 rpm) and air low (rate about 0.8 lit/min) were then started. The reaction was carried out at room temperature (25–35° C.) for 10 min. The reaction mass was then transferred to a separating funnel and the treated naphtha separated. The layer containing the catalyst was reused with fresh naphtha doped with 1-hexanethiol (100 ml). The catalyst solution was thus repeatedly used number of times. The mercaptan sulphur content of the treated naphtha obtained after each experiment was estimated by UOP method 163–89. Results are given in the following Table.

TABLE

Mercaptan in feed, 'S' ppmw: 533
Catalyst concentration on feed basis, ppmw: 81.5
Reaction time, min: 10
Air flow rate at NTP, litres/min: 0.3

| | Mercaptan in product 'S' ppmw | |
|---|---|---|
| Cumulative feed processed | Catalyst prepared by earlier method | Catalyst prepared by present method |
| 0.1 | 1.0 | 4.8 |
| 0.2 | 3.6 | 2.3 |
| 0.3 | 3.6 | 2.5 |
| 0.4 | 4.5 | 3.4 |
| 0.5 | 5.4 | 3.3 |
| 0.6 | 8.0 | 2.4 |
| 0.7 | 14.0 | 4.0 |
| 0.8 | 16.0 | 3.4 |
| 0.9 | 22.5 | 3.5 |
| 1.0 | 23.6 | 3.2 |
| 1.1 | | 2.5 |

TABLE-continued

Mercaptan in feed, 'S' ppmw: 533
Catalyst concentration on feed basis, ppmw: 81.5
Reaction time, min: 10
Air flow rate at NTP, litres/min: 0.3

| | Mercaptan in product 'S' ppmw | |
|---|---|---|
| Cumulative feed processed | Catalyst prepared by earlier method | Catalyst prepared by present method |
| 1.2 | | 3.1 |
| 1.3 | | 2.5 |
| 1.4 | | 2.4 |
| 1.5 | | 2.6 |
| 1.6 | | 3.9 |
| 1.7 | | 3.2 |
| 1.8 | | 2.4 |
| 1.9 | | 4.2 |
| 2.0 | | 3.2 |

Advantages of the Invention

The main advantages of the present invention over the previous inventions are:

(a) The present invention provides an improved process for the preparation of metal phthalocyanine sulphonamide sweetening catalysts from metal phthalocyanines in almost quantitative yields in contrast to the previous method, which gave 40–45 yield.

(b) Cobalt phthalocyanines sulphonarnide prepared from cobalt phthalocyanine following the method reported in this invention was found to be highly active catalyst for both liquid-liquid sweetening and alkali regeneration in the mercaptan extraction from various petroleum fractions.

(c) Cobalt phthalocyanine sulphonamide prepared according to this invention are not dusty and do not create handling problems as encountered with the conventional cobalt phthalocyanine disulphonate catalyst. Therefore, admixing with water to make slurry is not required.

(d) As the metal phthalocyanine sulphonamide described in this invention are insoluble in acidic media, their isolation is sulphonates.

What is claimed is:

1. An improved process for the preparation of metal phthalocyanines sulphonamides of the formula

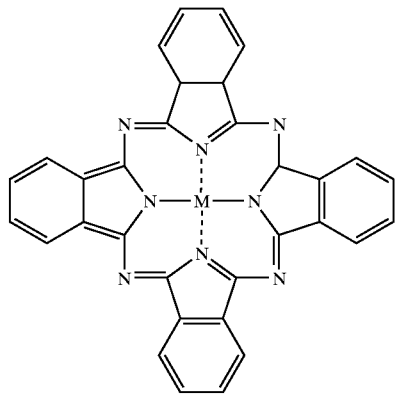

$MPc(SO_2NHR)_x$ wherein MPc represents useful as a catalyst for sweetening of LPG and light petroleum distillates which comprises;

reacting a metal phthalocyanine with chlorosulphonic acid at a temperature in the range of 90–150° C. for a period ranging between 1 hr–5 hrs, cooling the mixture to a temperature ranging between 40–80° C., adding 1–7 parts of a chloride reagent to the said mixture, heating the above said mixture to a temperature ranging between 60–80° C. for a period ranging between 0.5 hr to 3 hrs to obtain the metal phthalocyanine sulphonyl chloride, isolating the above said compound by adding the reaction mixture in an ice cold water, reacting the above isolated metal phthalocyanine sulphonyl chloride with an amine of general formula $H_2NR$ where R is selected from hydrogen, aryl, alkyl and cycloalkyl in an aqueous or non aqueous medium or a mixture thereof at a temperature in the range −4 to 15° C. and at a pH ranging between 7–9 in the presence of an acid binding agent to obtain the desired catalyst.

2. An improved process as claimed in claim 1, wherein the metal phthalocyanine used is selected from the group consisting of cobalt, manganese, iron, nickel, chromium and vanadium phthalocyanine, most preferably cobalt phthalocyanine.

3. An improved process as claimed in claim 1 wherein the chloride reagent used is selected from the group consisting of thionyl chloride, phosphorous trichloride and phosphorous trichloride and phosphorous pentachloride.

4. An improved process claimed in claim 1 wherein the non-aqueous medium used is selected from the group consisting of chlorobenzene, nitrobenzene, alcohols and N,N-dimethylformamide.

5. An improved process as claimed in claim 1 wherein the acid binding agent used is selected from the group consisting of sodium bicarbonate, sodium carbonate, sodium hydroxide and tertiary organic bases selected from pyridine, triethyl amine and piperidine.

6. An improved process as claimed in claim 1 wherein the—catalyst prepared is metal phthalocyanine sulphonamide selected from the group consisting of cobalt, manganese, nickel, iron, vanadium phthalocyanine sulphonamides.

7. An improved process as claimed in claim 2 wherein the chloride reagent used is selected from the group consisting of thionyl chloride, phosphorous trichloride and phosphorous trichloride and phosphorous pentachloride.

8. An improved process claimed in claim 2 wherein the non-aqueous medium used is selected form the group consisting of chlorobenzene, nitrobenzene, alcohols N,N-dimethylformamide.

9. An improved process as claimed in claim 3 wherein the non-aqueous medium used is selected from the group consisting of chlorobenzene, nitrobenzene, alcohols and N,N-dimethylformamide.

10. An improved process as claimed in claim 7 wherein the non-aqueous medium used is selected from the group consisting of chlorobenzene, nitrobenzene, alcohols and N,N-dimethylformamide.

11. An improved process as claimed in claim 2 wherein the acid binding agent used is selected from the group consisting of sodium bicarbonate, sodium carbonate, sodium hydroxide and tertiary organic bases selected from pyridine, triethyl amine and piperidine.

12. An improved process as claimed in claim 3 wherein the acid binding agent used is selected from the group consisting of sodium bicarbonate, sodium carbonate, sodium hydroxide and tertiary organic bases selected from pyridine, triethyl amine and piperidine.

13. An improved process as claimed in claim 4 wherein the acid binding agent used is selected from the group consisting of sodium bicarbonate; sodium carbonate, sodium hydroxide and tertiary organic bases selected from pyridine, triethyl amine and piperidine.

14. An improved process as claimed in claim 7 wherein the acid binding agent used is selected from the group consisting of sodium bicarbonate, sodium carbonate, sodium hydroxide and tertiary organic bases selected from pyridine, triethyl amine and piperidine.

15. An improved process as claimed in claim 8 wherein the acid binding agent used is selected from the group consisting of sodium bicarbonate, sodium carbonate, sodium hydroxide and tertiary organic bases selected from pyridine, triethyl amine and piperidine.

16. An improved process as claimed in claim 9 wherein the acid binding agent used is selected from the group consisting of sodium bicarbonate, sodium carbonate, sodium hydroxide and tertiary organic bases selected from pyridine, triethyl amine and piperidine.

17. An improved process as claimed in claim 10 wherein the acid binding agent used is selected from the group consisting of sodium bicarbonate, sodium carbonate, sodium hydroxide and tertiary organic bases selected from pyridine, triethyl amine and piperidine.

18. An improved process as claimed in claim 2 wherein the—catalyst prepared is metal phthalocyanine sulphonamide selected from the group consisting of cobalt, manganese, nickel, iron, vanadium phthalocyanine sulphonamides and their—substituted sulfonamide derivatives.

19. An improved process as claimed in claim 3 wherein the—catalyst prepared is metal phthalocyanine sulphonamide selected from the group consisting of cobalt, manganese, nickel, iron, vanadium phthalocyanine sulphonamide and their—substituted sulfonamide derivatives.

20. An improved process as claimed in claim 4 wherein the—catalyst prepared is metal phthalocyanine sulphonamide selected from the group consisting of cobalt, manganese, nickel, iron, vanadium phthalocyanine sulphonamide and their—substituted sulfonamide derivatives.

21. A process as claimed in claim 2 wherein the metal phthalocyanine is cobalt phthalocyanine.

22. A process as claimed in claim 1 wherein said catalyst is selected from cobalt phthalocyanine tetra-sulphonamide and cobalt phthalocyanine tetra-N15 4-hydroxy phenyl-sulphonamide.

* * * * *